United States Patent [19]

Travers et al.

[11] Patent Number: 4,950,471

[45] Date of Patent: Aug. 21, 1990

[54] ACETATE SELECTED BACILLUS THURINGIENSIS AND THE METHOD OF USE

[75] Inventors: Russell S. Travers, Takoma Park; Phyllis A. W. Martin, Lanham, both of Md.

[73] Assignee: The United States of America as represented by the Secretary of Agriculture, Washington, D.C.

[21] Appl. No.: 50,450

[22] Filed: May 18, 1987

[51] Int. Cl.$^5$ .................... A01N 63/00; C12N 15/01; C12N 1/22; C12N 3/00
[52] U.S. Cl. .................................. 424/93; 435/172.1; 435/172.3; 435/242; 435/252.5; 435/832
[58] Field of Search ...................... 424/93; 435/68, 70, 435/91, 170, 172.1, 172.3, 253, 822, 832; 935/59, 60, 61, 64

[56] References Cited

U.S. PATENT DOCUMENTS

| | | | |
|---|---|---|---|
| 3,702,359 | 11/1972 | Dulmage et al. | 424/93 |
| 3,758,383 | 9/1973 | Shieh et al. | 195/96 |
| 4,247,644 | 1/1981 | Sharpe et al. | 435/242 |
| 4,277,564 | 7/1981 | Johnson | 435/242 |
| 4,410,625 | 10/1983 | Cadmus | 435/42 |
| 4,695,455 | 9/1987 | Barnes et al. | 424/93 |

OTHER PUBLICATIONS

Salama et al., 1984 Z Angew Entomol, 97(1): 29–36, In: Biological Abstracts, 80(1): Abstr. No. 2649.

A. A. Yousten, "A Method for the Isolation of Asporogenic Mutants of *Bacillus thuringiensis*," *Can. J. Microbiol.* 24: 492–494, (1978).

K. W. Nickerson et al., "Physiology of Sporeforming Bacteria Associated with Insects: Minimal Nutritional Requirements for Growth, Sporulation, and Parasporal Crystal Formation of *Bacillus thuringiensis*," *Appl. Microbiol.*, 28: 124–128, (1974).

S. M. Saleh et al., "Method for Determining *Bacillus thuringiensis* var. *thuringiensis* Berliner in Soil," Can. J. Microbiol., 15: 1101–1103, (1969).

*Primary Examiner*—Robin L. Teskin
*Assistant Examiner*—Richard C. Peet
*Attorney, Agent, or Firm*—M. Howard Silverstein; Beverly K. Johnson

[57] ABSTRACT

Methods and mutant *Bacillus thuringiensis* strains are provided for controlling lepidopteran insects. Sporogenic, crystalliferous mutant strains for *B. thuringiensis* having the identifying characteristics of NRRL B-18195, NRRL B-18196 and NRRL B-18197 are provided for use as biocontrol agents. Said strains have the ability to produce a bypyramidal crystal composed of toxic protein and require a leucine and valine containing nutrient medium for growth, sporulation and crystal production.

14 Claims, No Drawings

ACETATE SELECTED BACILLUS THURINGIENSIS AND THE METHOD OF USE

BACKGROUND OF THE INVENTION

1. Field of the Invention

The present invention relates to novel biological insecticides. More specifically, this invention relates to novel strains of *Bacillus thuringiensis,* "*B. thuringiensis,*" the method of their production and the method of use thereof as biological insecticides to control insect species of the order of Lepidoptera, in particularly the *Trichoplusia ni,* "the cabbage looper" and the *Artogeia rapae,* "the imported cabbageworm."

2. Description of the Prior Art

The spore forming microorganism *B. thuringiensis* was isolated over 80 years ago and has since become commercially prominent for biological control. The sporulating cells of *B. thuringiensis* each produce a spore (endospore) and a diamond-shaped proteinaceous crystal (paraspore or inclusion body). The entomocidal properties have been attributed solely to the δ-endotoxin which is a major component of the parasporal crystal. When the crystal solubilizes in the insect gut, it gives rise to a protoxin which is activated by proteolytic digestion.

Although quite specific for lepidopteran insects and certain flies and mosquitoes, *B. thuringiensis* is harmless to non-susceptible orders of insects, animal and man. Currently in the United States, *B. thuringiensis* var. *kurstaki* comprises the *B. thuringiensis* insecticidal products most widely-used for control of these pests. However, these products lack effective control at economical levels of application.

On the other hand, synthetic pyrethroids are the chemical insecticidal agents most widely-used for control of lepidopteran pests. Pyrethroids are highly effective and offer increased control over the currently used *B. thuringiensis* insecticidal products. A disadvantageous feature associated with the use of pyrethroids, however, lies in the fact that they are toxic to non-targeted invertebrates, thereby, presenting an environmental hazard to aquatic life. Consequently, there exists a need for effective lepidopteran-active insecticides which are environmentally safe and cost effective, and which duplicate the efficacy of synthetic pyrethroids.

SUMMARY OF THE INVENTION

An object of the present invention is to provide novel strains of the microorganism, *B. thuringiensis* which are highly effective for the biological control of insects of the Lepidoptera order.

Another object of this invention is to provide novel strains of *B. thuringiensis* having a toxigenic activity equal to synthetic pyrethroids or greater than previously used *B. thuringiensis* insecticidal products.

Still another object is to provide a method of biologically controlling the cabbage looper and the imported cabbageworm.

Viable cultures of the novel strains of *B. thuringiensis* have been deposited with the culture collection at the Northern Regional Research Center, U. S. Department of Agriculture, Peoria, Illinois, 61604, and their accession numbers are NRRL B-18195, NRRL B-18196, and NRRL B-18197. Progenies of these strains will be available during the pendency of the patent application to one determined by the Commissioner of Patents and Trademarks to be entitled thereto under 37 CFR 1.14 and 35 USC 122. All restrictions on the availability of progenies of these strains to the public will be irrevocably removed upon the granting of the patent of which the strains are the subject.

The novel strains are sporogenic, crystalliferous, mutant strains of environmentally isolated *B. thuringiensis* and have the ability to produce bypyramidal crystals composed of toxic protein and are unique in that they possess an auxotrophy requiring a leucine and valine amino-acid complex for growth, sporulation and crystal production. In contrast, previously observed strains of *B. thuringiensis* have exhibited an auxotrophy that can be satisfied without an amino acid. K. W. Nickerson et al. [Appl. Microbiol. 28: 124–128 (1974)].

DETAILED DESCRIPTION OF THE INVENTION

For purposes of this invention, the term "auxotrophy" is defined herein to mean the nutritional requirements necessary for growth, sporulation and crystal production of the microorganism.

The phrase "complex amino acid medium" is defined herein to designate a medium comprising a combination of two or more amino acids.

The novel strains NRRL B-18195, NRRL B-18196 and NRRL B-18197 are generated from the soil using a non-classical sodium acetate-heat selection process. In accordance with this procedure, an aqueous nutrient medium is buffered to about 0.25M with sodium acetate to permit germination only of undesirable sporeforming organisms present in an environmental soil sample. Next, the vegetated sporeforming organisms and the non-sporeforming organisms in the sample are killed by heat treatment. The surviving spores are thereafter plated and grown on a suitable agar medium to obtain the novel strains of the invention. Without desiring to be bound to any particular theory, it is believed that the novel strains of the invention are produced during the selection process as a result of mutagenesis of naturally occuring *B. thuringiensis* strains with consecutive treatments of sodium acetate and heat.

An example of the selection procedure is as follows: 0.5 grams of soil were added to 10 mls of L-broth (100 mls $H_2O$, 1 g tryptone; 0.5 g yeast extract, 0.5 g NaCl) in a 125 ml baffled flask. The L-broth was buffered to 0.25M with sodium acetate. The mixture was shaken for 4 hrs at 250 rpm at 30° C. Using a flow-through pasturization heat treater, the mixture was then heated at 80° C. for 3 minutes. The heat-treated mixture was plated on L-agar (L-broth solidified with 1.5% agar) and incubated overnight (16 hrs) at 30° C.

Strains NRRL B-18195, NRRL B18196 and NRRL B-18197 have the following characteristics: Colonies are circular, entire, convex, and cream color with a colony diameter of 2-7 mm on nutrient agar after 24 hours. The vegetative cells are aerobic, gram positive, motile rods measuring 1 $\mu$m to 1.2 $\mu$m by 3 $\mu$m to 5 $\mu$m. The terminal spores of the vegetative cells do not distend the sporangia and are 33% to 50% of the vegetative rods. The cells are catalase positive, ferment glucose, hydrolyse casein, but unlike the taxonomic description of the previously observed *B. thuringiensis* strains, the strains of the invention do not utilize citrate. The novel strains also do not ferment mannitol, arabinobe and xylose.

In addition, strain NRRL B-18195 hydrolyzed starch, fermented sucrose and produced a lecithinase; the cells did not utilize esculin, did not produce a urease and did not ferment salicin and mannose. Strain NRRL B-18196 hydrolyzed starch and fermented salicin, mannose and sucrose; the cells did not utilize esculin and did not produce a urease or a lecithinase. Strain NRRL B-18197 hydrolyzed starch, utilized esculin, produced a lecithinase and fermented salicin; the cells did not produce a urease and did not ferment mannose or sucrose. All three strains are resistant to penicillin-type antibiotics, such as naficillin, ampicillin and methicillin, and are resistant to low levels, i.e. about 10 g/ml, of neomycin, kanamycin and ethidium bromide.

As mentioned previously, the production of spores and proteinaceous crystals of B. thuringiensis strains having the characteristics of NRRL B-18195, NRRL B-18196 and NRRL B-18197 require an aqueous nutrient medium which contains a leucine-valine amino acid complex. For optimum crystal production of the invention bacteria, the specifically preferred media composition is the following: 0.3% tryptone, 0.2% tryptose, 0.45% yeast extract made 0.01M in sodium phosphate buffer at pH 6.8 with the addition of $10^{-8}$M MgSO$_4$ and $10^{-9}$M MnSO$_4$ after autoclaving. Other appropriate medium having the required amino acid complex may be used for growth of the bacteria of the invention. However, media used other than the preferred medium may result in a diminished crystal production.

Production of the cells is effected under aerobic conditions at any temperature satisfactory for growth of the organisms of the invention, i.e. from about 10° C. to 40° C.; the preferred temperature range is about 27° C. to 32° C. The pH of the nutrient media suitable for growing the B. thuringiensis culture is about neutrality, i.e. pH 6.7 to 7.2. Incubation time is that time necessary for complete spore and crystal liberation and is preferably about 18 to 24 hours. Cells may be grown in any conventional baffled shake flask for small runs. For larger scale operations, it is convenient to carry out the culture in a tank, applying agitation and aeration to the inoculated liquid medium. After incubation, the cells are harvested by conventional sedimentation methodology such as centrifugation or filtering. The cells may be used as is or frozen for later use.

Mutant B. thuringiensis strains, NRRL B-18195, NRRL B-18196 and NRRL B-18197 are highly effective insecticides and may be used in programs to control insects of the lepidopteran order, in particularly the cabbage looper and the imported cabbageworm. The strains may be used in formulations with an inert liquid carrier, such as water. Optionally, the strain formulations may contain conventional additives such as stickers, spreaders, emulsifiers, surfactants and extenders. The strain formulation may be sprayed using conventional spraying techniques and devices. The novel strains can also be encapsulated or entrapped in a suitable encapsulation material, such as an organic polymer, and applied in powder form. It is also contemplated that the genetic material for the δ-endotoxin of the novel B. thuringiensis strains of the invention may be transferred, using recombinant DNA techniques, to other bacteria and plants in order to provide increased insect control.

It is within the compass of this invention to use the novel strains alone or in combination with other control agents, such as insecticides and attractants. When used, these agents should be used in an amount, as readily determined by one skilled in the arts, which will not interfere with the effectiveness of the biological insecticidal material of the invention.

The following example is intended to further illustrate the invention and not to limit the scope of the invention as defined by the claims.

EXAMPLE I

In a field test, the effectiveness of B. thuringiensis strains NRRL B-18195, NRRL B-18196 and NRRL B-18197 against the cabbage looper and the imported cabbageworm was compared to the effectiveness of the synthetic pyrethroid-containing insecticidal product, "Pydrin" and the B. thuringiensis, var kurstaki insecticidal product, "Dipel." "Pydrin" is the Tradename for a product sold by Shell Corporation and contains 30% cyano(3-phenoxyphenyl) methyl-4-chloro-alpha(1-methylethyl) benzeneacetate and 70% inert ingredients. "Dipel" is the Tradename of a product sold by Abbott Laboratories and contains 3.2% of B. thuringiensis, var. kurstaki and 98.8% inert ingredients.

On the Eastern Shore of Maryland collards were direct seeded in 4 row plots 20 ft. long on July 7, 1986. Plants were spaced 2 inches apart in the row and 36 inches between rows. The treatments were arranged in a randomized complete block design with 4 replications. Each row was buffered by a guard row. The soil was a Norfolk "A" loamy sand. All spray treatments were $5.5 \times 10^9$ spore equivalent per 0.5 liter of water to which 0.01% of liquid detergent was added as a spreader. Spray treatments were applied with a trombone type garden sprayer calibrated to deliver 30 gal./acre of the formulation.

The rows were treated with applications on August 11, 18 and 25 and September 2 and 8. On September 15, the foliage injury ratings and insect counts were taken. Insect pressure from naturally occurring infestation of the cabbage looper and the imported cabbageworm was moderate. Foliage injury ratings ranged from 1-5 and were indexed as following: (1) 0-3% damage—odd holes on leaves; (2) 4-10% damage—few leaves with holes; (3) 11-25% damage—moderate number of leaves with holes; (4) 26-50% damage—most leaves with holes; and (5) 51-100% damage—crown damage and/or all leaves with holes.

Data was analyzed by analysis of variance, and means were separated by Duncan's multiple range test (DMRT) at the $P=0.05$ level (Duncan 1951). The results are recorded in the Table below.

The table clearly shows the excellent insecticidal properties of the novel strains of the invention against the cabbage looper and the imported cabbageworm. B. thuringiensis strain NRRl-18197 provided statistically the same protection for the collards as "Pydrin." Clearly, strains NRRL B-18195 and NRRL B-18196, which showed identical levels of protection in terms of mean foliage damage, were both statistically inferior to "Pydrin." These novel strains, however, provided a 10-fold increase in activity over the commercial B. thuringiensis product, "Dipel." Such an increase was well demonstrated where "Dipel" treatments displayed the identical level of control (less than 10% damage) as strain NRRL B-18195 at 1:10 dilution.

It is understood that modification and variation may be made to the foregoing disclosure without departing from the spirit and scope of the invention.

| Treatment and rate/acre | Mean no. T. ni per 10 plants[1] 15 Sep | Mean no. A. rapae per 10 plants[1] 15 Sep | Mean foliage injury rating[1,2,3] 15 Sep |
|---|---|---|---|
| Pydrin 2.4 EC 0.21b(AI)/acre | 0.0a | 0.0a | 1.00a |
| NRRL B-18197 B. thuringiensis[5] | 0.50abc | 1.0abc | 1.25a |
| NRRL B-18195 B. thuringiensis[5] | 1.25abc | 1.25abc | 2.00b |
| NRRL B-18196 B. thuringiensis[5] | 0.25ab | 1.0abc | 2.00b |
| 1/10 B-18195 B. thuringiensis[5] | 0.75abc | 3.0e | 2.75cde |
| Dipel 1.01 lb[4] | 2.25cde | 2.25de | 2.50bcd |
| Untreated check | 4.75g | 4.50g | 4.0g |

[1]Any two numbers in the same column followed by the same letter are not significantly different (P = 0.05) DMRT.
[2]Sprayed 11, 18, 25, Aug; 2, 8 Sep.
[3]Damage caused predominantly by cabbage looper and imported cabbageworm.
[4]Dipel = 7.26 billion international units per pound.
[5]Calibrated to yield 7.26 billion international units per pound.

We claim:

1. A culture of a sporogenic, crystalliferous mutant of *Bacillus thuringiensis* having the identifying characteristics of a strain selected from the group consisting of NRRL B-18195, NRRL B-18196 and NRRL B-18197, wherein said strain is characterized as having the ability to produce bypyramidal crystals composed of toxic protein and requiring a leucine and valine containing nutrient medium for growth, sporulation and crystal production.

2. A culture as described in claim 1 wherein said strain has the identifying characteristics of NRRL B-18195.

3. A culture as described in claim 1 wherein said strain has the identifying characteristics of NRRL B-18196.

4. A culture as described in claim 1 wherein said strain has the identifying characteristics of NRRL B-18197.

5. A biocontrol agent for controlling lepidopteran insects comprising a culture of a sporogenic, crystalliferous mutant of *Bacillus thuringiensis* having the identifying characteristics of a strain selected from the group consisting of NRRL B-18195, NRRL B-18196 and NRRL B-18197, wherein said strain is characterized as having the ability to produce a bypyramidal crystal composed of toxic protein and requiring a leucine and valine containing nutrient medium for growth, sporulation and crystal production.

6. A biological control agent of claim 5 wherein said strain has the identifying characteristics of NRRL B-18195.

7. A biological control agent of claim 5 wherein said strain has the identifying characteristics of NRRL B-18196.

8. A biological control agent of claim 5 wherein said strain has the identifying characteristics of NRRL B-18197.

9. A method for controlling lepidopteran insects comprising subjecting the insects to an effective insecticidal amount of a sporogenic, crystalliferous mutant of *Bacillus thuringiensis* having the identifying characteristics of a strain selected from the group consisting of NRRL B-18195, NRRL B-18196 and NRRL B-18197, wherein said strain is characterized as having the ability to produce bypyramidal crystals composed of toxic protein and requiring a leucine and valine containing nutrient medium for growth, sporulation and crystal production.

10. A method of claim 9 wherein said strain has the identifying characteristics of NRRL B-18195.

11. A method of claim 9 wherein said strain has the identifying characteristics of a strain of NRRL B-18196.

12. A method of claim 9 wherein said strain has the identifying characteristics of NRRL B-18197.

13. A method of claim 9 wherein said strain is contained in an inert liquid carrier.

14. A method of claim 9 wherein said lepidopteran insects are selected from the group consisting of *Trichoplusia ni* and *Artogeia rapae*.

* * * * *